(12) United States Patent
Sanchez et al.

(10) Patent No.: US 6,436,090 B1
(45) Date of Patent: Aug. 20, 2002

(54) MULTI LUMEN CATHETER SHAFT

(75) Inventors: Diana M. Sanchez, Santa Clara;
Barbara E. Stamberg, San Jose, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/745,828

(22) Filed: Dec. 21, 2000

(51) Int. Cl.[7] ................. A61M 25/10; A61M 25/16
(52) U.S. Cl. ..................... 604/525; 604/96.01
(58) Field of Search ................. 604/96.01, 525

(56) References Cited

U.S. PATENT DOCUMENTS

| | | | | |
|---|---|---|---|---|
| 5,261,819 A | * | 11/1993 | Brill | 604/96.01 |
| 5,480,383 A | * | 1/1996 | Bagaolsan et al. | 604/525 |
| 5,522,808 A | * | 6/1996 | Keith et al. | 604/525 |
| 5,743,875 A | | 4/1998 | Sirhan et al. | 604/96 |
| 6,004,291 A | * | 12/1999 | Ressemann et al. | 604/525 |
| 6,027,475 A | * | 2/2000 | Sirhan et al. | 604/96.01 |
| 6,027,477 A | * | 2/2000 | Kastenhofer | 604/96.01 |
| 6,077,258 A | * | 6/2000 | Lange et al. | 604/525 |
| 6,102,931 A | * | 8/2000 | Thornton | 604/96.01 |
| 6,179,788 B1 | * | 1/2001 | Sullivan | 604/96.01 |
| 6,179,810 B1 | * | 1/2001 | Wantink et al. | 604/96.01 |

* cited by examiner

*Primary Examiner*—Paul J. Hirsch
(74) *Attorney, Agent, or Firm*—Fulwider Patton Lee & Utecht, LLP (57) ABSTRACT

The invention is generally directed to an intraluminal catheter systems including an elongated shaft having proximal and distal shaft sections, and an inflatable member disposed on the distal shaft section and having an interior chamber. A guidewire receiving lumen extends along at least a portion of the proximal shaft section and at least a portion of the distal shaft section and extends distally to the shaft distal end. An inflation lumen extends along at least a portion of the proximal shaft section and at least a portion of the distal shaft section to a point proximal to a shaft distal end and is in fluid communication with the inflatable member interior chamber. The proximal shaft section has multiple non-concentric lumens with at least one lumen forming at least a portion of the guidewire receiving lumen and at least one lumen forming at least a portion of the inflation lumen.

20 Claims, 10 Drawing Sheets

MULTI LUMEN CATHETER SHAFT

FIELD OF INVENTION

The invention relates to the field of intravascular catheters, and particularly to a catheter suitable for angioplasty and/or stent deployment, and the like.

BACKGROUND OF THE INVENTION

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to keep open a stenosed vessel, and strengthen the dilated area by remaining inside the vessel. Instead of first using one catheter to dilate the body lumen and a second catheter to deploy the stent after the dilatation, the stent may be mounted on a balloon catheter and deployed at the same time the balloon is inflated to dilate the stenotic region.

Conventional balloon catheters for intravascular procedures, such as angioplasty and stent delivery, frequently have relatively stiff proximal shaft sections to facilitate advancement of the catheter within the patient's body lumen and a relatively flexible distal shaft sections to facilitate passage through tortuous anatomy such as distal coronary and neurological arteries without damage to the luminal wall. Typically, there is an intermediate shaft section or junction between the relatively stiff proximal shaft section and the relatively flexible distal shaft section which provides a transition between the proximal shaft section and less flexible than the distal shaft section.

A variety of shaft or junction designs have been utilized to enhance the transition between the more stiff proximal shaft and the more flexible distal shaft sections. However, what has been needed is a catheter with enhanced transition and improved overall and distal trackability, as well as improved inflation/deflation performance. The present invention satisfies these and other needs.

SUMMARY OF THE INVENTION

The invention is generally directed to an intraluminal catheter system with an improved transition between a proximal shaft portion and a more flexible distal shaft portion. The improvement provides enhanced flexibility and kink-resistance, thus, facilitating advancement through tortuous anatomy. The present catheters may be used for either or both angioplasty and stent deployment.

The catheters of the present invention includes an elongated shaft having proximal and distal shaft sections, an inflatable member disposed on the distal shaft section and having proximal and distal ends and an interior chamber. A guidewire receiving lumen extends along at least a portion of the proximal shaft section and at least a portion of the distal shaft section and extends distally to the shaft distal end. An inflation lumen extends along at least a portion of the proximal shaft section and at least a portion of the distal shaft section to a point proximal to a shaft distal end and is in fluid communication with the inflatable member interior chamber. The proximal shaft section has a plurality of tubular members forming non-concentric lumens with at least one lumen forming at least a portion of the guidewire receiving lumen and at least one lumen forming at least a portion of the inflation lumen.

The proximal shaft section has multiple non-concentric lumens with at least one lumen forming at least a portion of the guidewire receiving lumen and at least one lumen forming at least a portion of the inflation lumen. In one embodiment, there are at least three non-concentric lumens while in another embodiment there are at least four such lumens. The distal shaft section includes an outer tubular member with a proximal extremity disposed about and securely attached to a distal extremity of the proximal In one embodiment, the proximal extremity of the outer tubular member forms a seal with at least a portion of each of the proximal shaft lumens.

In a presently preferred embodiment, all of the proximal shaft lumens except the guidewire lumen are non-guidewire receiving lumens circumferencially disposed about the guidewire receiving lumen. Preferably, the multiple non-concentric lumens are disposed such that the transverse centers of the non-guidewire receiving lumens form a triangular arrangement.

Preferably, the non-guidewire lumens are inflation lumens usable in the delivery of all fluids, such as inflation fluids, to and from the catheter. In a preferred embodiment, the non-guidewire lumens are longitudinally set apart with the guidewire receiving lumen extending distally beyond the non-guidewire lumens.

In one embodiment, the distal shaft section includes an inner tubular member extending along at least a portion of the outer tubular member to the shaft distal end. The inner tubular member forms at least a portion of the guidewire receiving lumen in the distal shaft section and defines with the outer tubular member at least a portion of the inflation lumen.

In another embodiment, the guidewire receiving lumen includes a proximal guidewire receiving lumen, and a distal guidewire receiving lumen formed by the inner tubular member in the distal shaft section, with the two guidewire lumens being in fluid communication with one another.

In an embodiment, a proximal extremity of the inner tubular member is sealingly disposed about a distal extremity of the proximal guidewire lumen and forming a junction therebetween.

In another embodiment, the inner tubular member extends proximally within the proximal guidewire receiving lumen to the shaft proximal end.

In a presently preferred embodiment, a reinforcing member, such as a coil, extends within at least a portion of the guidewire receiving lumen, preferably, within at least a portion of the guidewire receiving lumen extending in the distal shaft section.

The outer tubular member can be tapered the distal direction. The tapering of the outer tubular member can be continuous or in steps.

The catheter of the present invention provides an improved design with superior pushability in the proximal shaft section, a greater degree of flexibility in the distal shaft section for more distal advancement of the catheter and an intermediate shaft section with a smoother, more flexible transition between the proximal and distal shaft sections.

Additionally, the catheters of the present invention provide enhanced deflation/inflation performance as well as improved reliability, as for example, little or no inner member collapse. Furthermore, the present invention provides a more balanced distribution of the inflation/deflation lumens, hence, improved guide wire movement within the guide wire lumen.

These and other advantages of the invention will become more apparent from the following detailed description of the invention and the accompanying exemplary drawings.

DETAILED DESCRIPTION OF THE INVENTION

FIGS. 1 through 6 illustrate an intravascular catheter 10 embodying features of the invention and generally including an elongated catheter shaft 13 with a proximal shaft section 16, a distal shaft section 19, and a radially expansive inflatable balloon 22 with an interior chamber 25 on a distal portion 28 of the distal shaft section 19. An adapter 31 is shown mounted on a proximal end 34 of the proximal shaft section 16.

The proximal shaft section 16 includes a plurality of lumens 37 extending from the proximal end 34 of the proximal shaft section 16 to at least a proximal portion 40 of the distal shaft section 19. One of the lumens 37 is a guidewire lumen 43 extending distally to a shaft distal end 46 for slidably receiving a guidewire 49 therein. At least one of a remaining lumens 52, which are not guidewire lumens, forms at least part of an inflation lumen 55 extending along at least a portion of the proximal shaft section 16 to a point within the distal shaft section 19. Preferably, the non-guidewire lumens 52, or as used herein forward, inflation lumens, include a plurality of the inflation lumens 55, more preferably, as many as there are lumens 37 less the guidewire lumen 43, as for example, inflation lumens 58, 61, and 64, shown in FIG. 1. It should be understood by those skilled in the art, that inflation lumen 55 is meant to include a lumen used for both inflation and/or deflation of the inflatable member 22, as well as, lumens used separately for inflation, deflation, or any other fluid delivery, to and from the shaft 13.

Figure 5A:
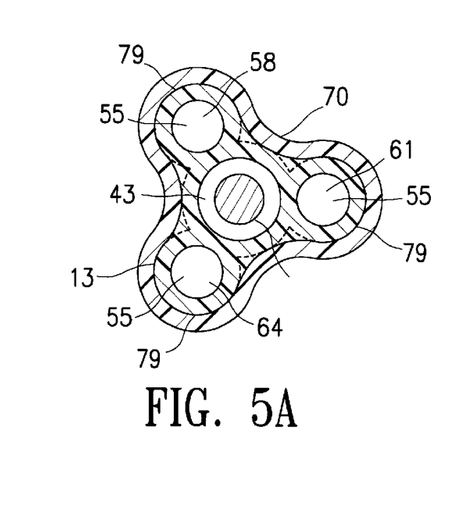
FIG. 5A is a transverse cross sectional view of the catheter system of FIG. 1 taken along lines 5A—5A.
Figure 5B:
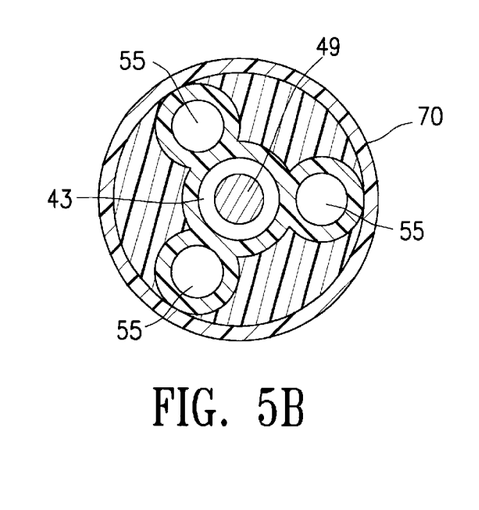
FIG. 5B is a transverse cross sectional view of another embodiment of the catheter system of FIG. 1 taken along lines 5B—5B showing the junction.
Figure 6:
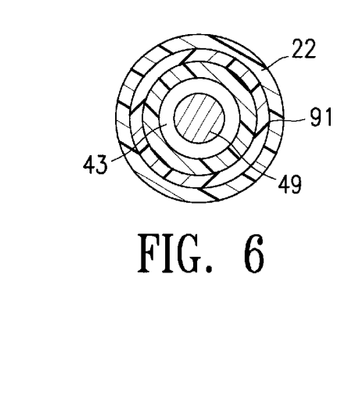
FIG. 6 is a transverse cross sectional view of the catheter system of FIG. 1 taken along lines 6—6.

The distal shaft section 19 includes an outer tubular member 67 having a proximal extremity 70 disposed about and securely attached to a distal extremity 73 of the proximal shaft section 16 at a junction 76. Preferably, in the embodiment shown in FIG. 1, the outer tubular member 67 forms a seal 79 with at least a portion of the exterior of the non-guidewire lumens 52, preferably, also the guidewire lumen 43. The seal at the junction 76 can be formed in any suitable form, such as a laser seal (FIG. 5A) or an adhesive seal (FIG. 5B). The distal shaft section 19 further includes at least a portion of the guidewire lumen 43. A single annular inflation lumen 82, defined at least in part, by the outer tubular member 67 and at least a portion of the exterior of the guidewire lumen 43 is in fluid communication with at least one of the inflation lumens 55 and extends to a location spaced proximal to the distal end 46 of the catheter shaft 13.

Figure 1:
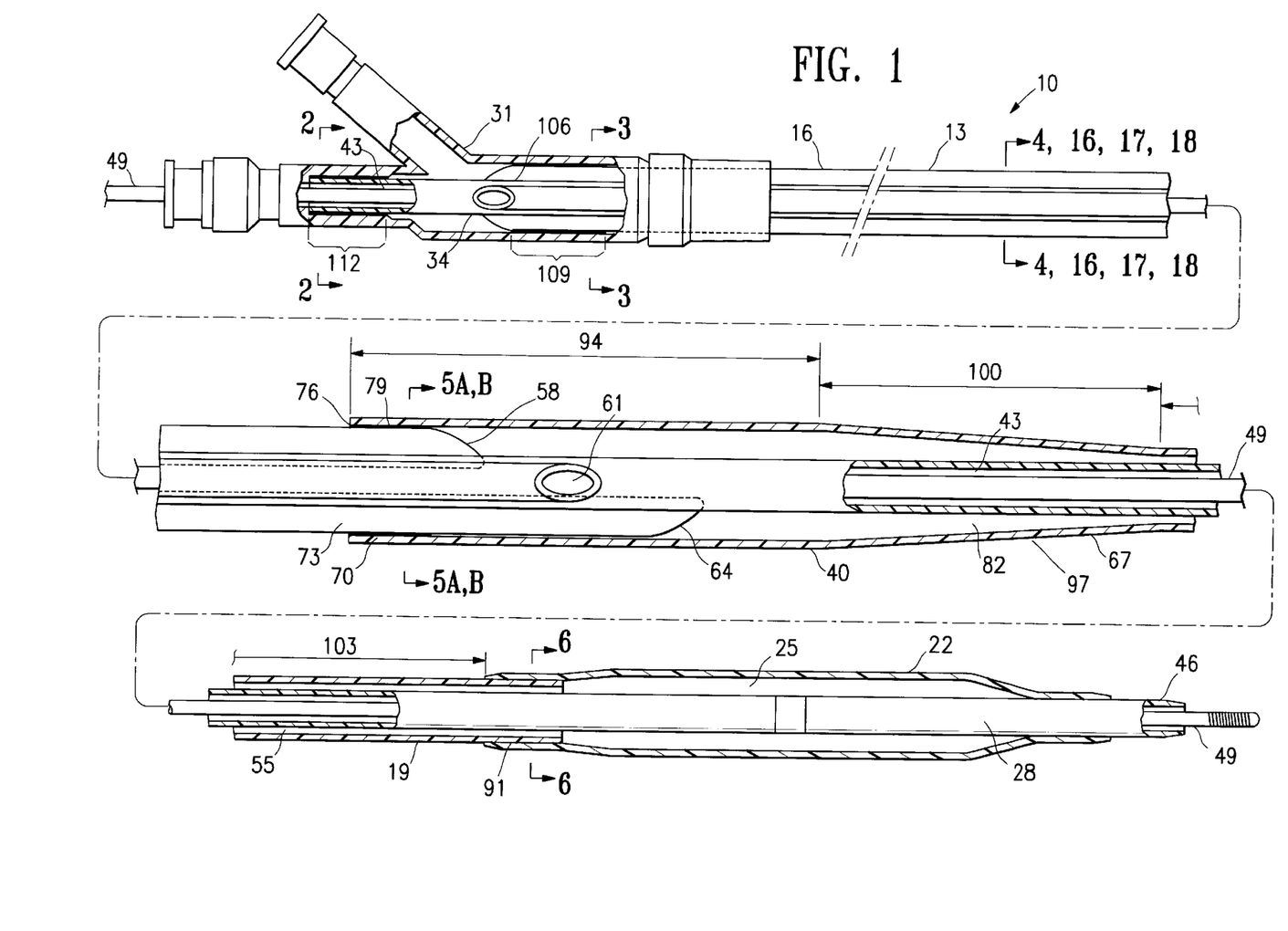
FIG. 1 is a schematic, elevational view, partially in section, of a catheter system embodying features of the invention.
Figure 2:
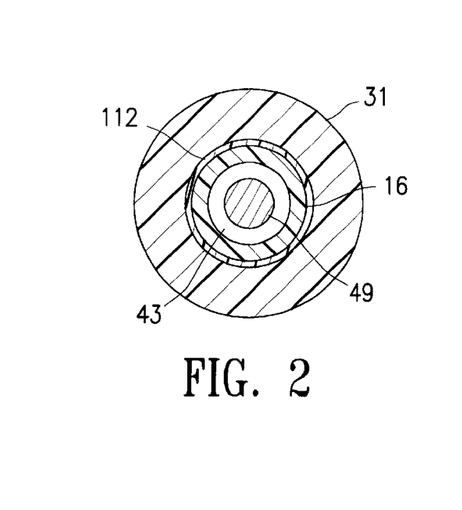
FIG. 2 is a transverse cross sectional view of the catheter system of FIG. 1 taken along lines 2—2.
Figure 3:
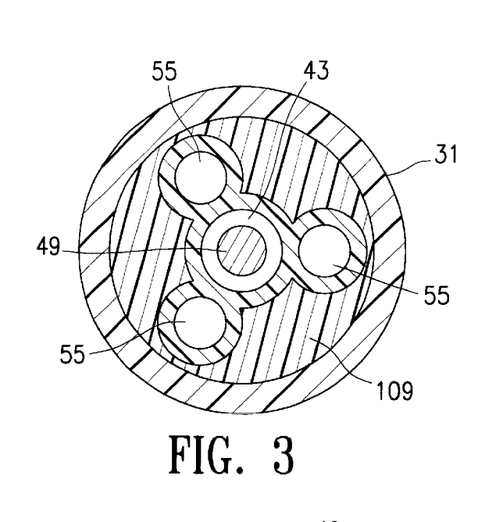
FIG. 3 is a transverse cross sectional view of the catheter system of FIG. 1 taken along lines 3—3.
Figure 4:
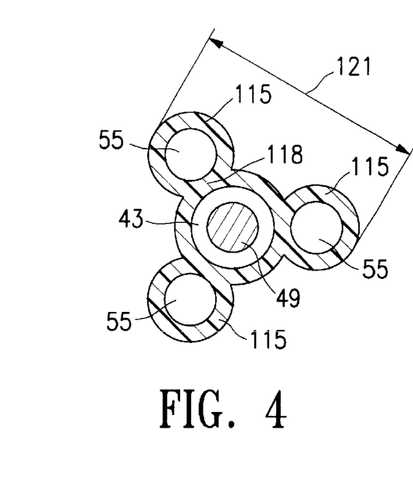
FIG. 4 is a transverse cross sectional view of the catheter system of FIG. 1 taken along lines 4—4.

The distal shaft section 19, optionally, along its proximal portion 40 extending from a distal shaft section proximal end to a proximal balloon seal 91 can be tapered in the distal direction to a smaller transverse dimension, to include a first non-tapered portion 94 followed by a tapering portion 97. The tapering portion 97 may be a continuous taper, or in the alternative, include non-tapering segments. As shown in FIG. 1, the tapering portion 97 includes a tapered segment 100, with a non-tapered segment 103, disposed distal to the tapered segment 100.

The lumens 37 at a proximal portion 106 thereof form a distal seal 109 with the adapter 31. Additionally, the guidewire lumen 43, extends, further proximally forming a proximal seal 112 with the adapter 31.

The inflation lumens 55 are circumferentially disposed about the guidewire lumen 43. Preferably, the center of each of the inflation lumens 55 is 120° apart from the center of an adjacent inflation lumen 55. In a presently preferred embodiment, a wall thickness 115 of each of the inflation lumens 55 is substantially the same, including a wall thickness 118 between the guidewire lumen 43 and an adjacent inflation lumen 55.

In the embodiment of FIG. 1 (e.g., FIG. 4), the outer surface of each of the adjacent inflation lumens 55 is set apart from an adjacent inflation lumen 55 such that the inflation lumens 55 are not in an abutting relationship with one another. However, it should be appreciated by those skilled in the art that the inflation lumens 55 may be of a dimension such that their exterior walls may come into contact with one another, as for example shown in other embodiments such as FIG. 15 below.

The catheter 10 of the present invention has a longitudinal dimension ranging from about 135 cm to about 145 cm, preferably from about 142 cm to about 144 cm, normally 143 cm.

The proximal shaft section 16 has a longitudinal dimension ranging from about 90 cm to about 120 cm, preferably from about 100 cm to about 115 cm, normally 110 cm.

Distal and proximal adapter seals 109 and 112, respectively, have a longitudinal dimension ranging from about 0.8 cm to about 1.2 cm, preferably, from about 0.9 cm to about 1.0 cm.

The seal 79 between the proximal extremity 70 of the outer tubular member 67 and the distal extremity 73 of the proximal shaft section 16, has a longitudinal dimension ranging from about 0.5 cm to about 1.5 cm, preferably, from about 0.5 cm to about 0.7 cm.

In a presently preferred embodiment, the inflation lumens 55 are circular with a uniform wall thickness and having an inner diameter ranging from about 0.008 inch to about 0.020 inch, more preferably, from about 0.09 inch to about 0.011 inch; and an outer diameter ranging from about 0.014 inch to about 0.026 inch, more preferably, from about 0.015 inch to about 0.017 inch.

Preferably, the guidewire lumen 43 has an inner diameter ranging from about 0.014 inch to about 0.022 inch, more preferably, from about 0.016 inch to about 0.018 inch; and an outer diameter ranging from about 0.020 inch to about 0.028 inch, more preferably, from about 0.022 inch to about 0.024 inch.

The proximal shaft section 16 at its greatest transverse dimension 121, has a dimension ranging from about 0.040 inch to about 0.076 inch, preferably, from about 0.042 inch to about 0.048 inch. The inflation lumens 55, preferably, are longitudinally set apart and terminate within the outer tubular member 67, at a point distal to the junction 76, with the guidewire lumen 43 extending the farthest distally. In the embodiment features of which illustrated in FIGS. 1 and 6, the guidewire lumen 43 extends distally to the distal end 46 of the shaft 13.

The shortest inflation lumen 58 extends within the outer tubular member 67 in a range from about 1.5 cm to about 2.5 cm, preferably, from about 1.0 cm to about 2.0 cm, typically, 1.5 cm. The inflation lumens 55 are longitudinally set apart from each other in a range from about 1.5 cm to about 3.0 cm, preferably, from about 2.0 cm to about 2.5 cm, typically 2.0 cm.

The distal shaft section 19 has a longitudinal dimension ranging from about 15 cm to about 50 cm, preferably from about 25 cm to about 45 cm, normally 35 cm.

The proximal portion 40 of the distal shaft section 19, has a longitudinal dimension ranging from about 12 cm to about 50 cm, preferably, ranging from about 22 cm to about 42 cm, typically, about 25 cm. When tapered, the first non-tapered portion 94 has a longitudinal dimension ranging from about 5 cm to about 50 cm, preferably, from about 5 cm to about 15 cm, typically 5 cm; the tapering portion 97 has a longitudinal dimension ranging from about 5.0 cm to about 45 cm, preferably, from about 7 cm to about 25 cm, typically 7.5 to 10 cm; with the first tapered segment 100 having a longitudinal dimension ranging from about 5 cm to about 20 cm, preferably, from about 7.5 cm to about 10 cm, typically 7.5 cm; and the non-tapered segment 103 having a longitudinal dimension ranging from about 1 cm to about 25.0 cm, preferably, from about 19 cm to about 21 cm, typically 20 cm.

The distal shaft section 19 has a first transverse outer dimension (i.e., outer diameter) at the non-tapered portion 94 ranging from about 0.042 inch to about 0.080 inch, preferably, from about 0.045 inch to about 0.052 inch, typically 0.050 inch, with a tapering outer diameter along the first tapered segment 100, and tapering to a distal outer diameter at the non-tapered segment 103 of the tapering portion 97 ranging from about 0.030 inch to about 0.050 inch, typically 0.032 inch.

The distal shaft section 19 has a first inner diameter at the non-tapered portion 94 ranging from about 0.038 inch to about 0.076 inch, preferably, from about 0.040 inch to about 0.050 inch, typically 0.045 inch, with a tapering inner diameter along the first tapered segment 100, and tapering to a distal inner diameter at the non-tapered segment 103 of the tapering portion 97 ranging from about 0.026 inch to about 0.030 inch, typically 0.028 inch.

Figures 7A, 7B:
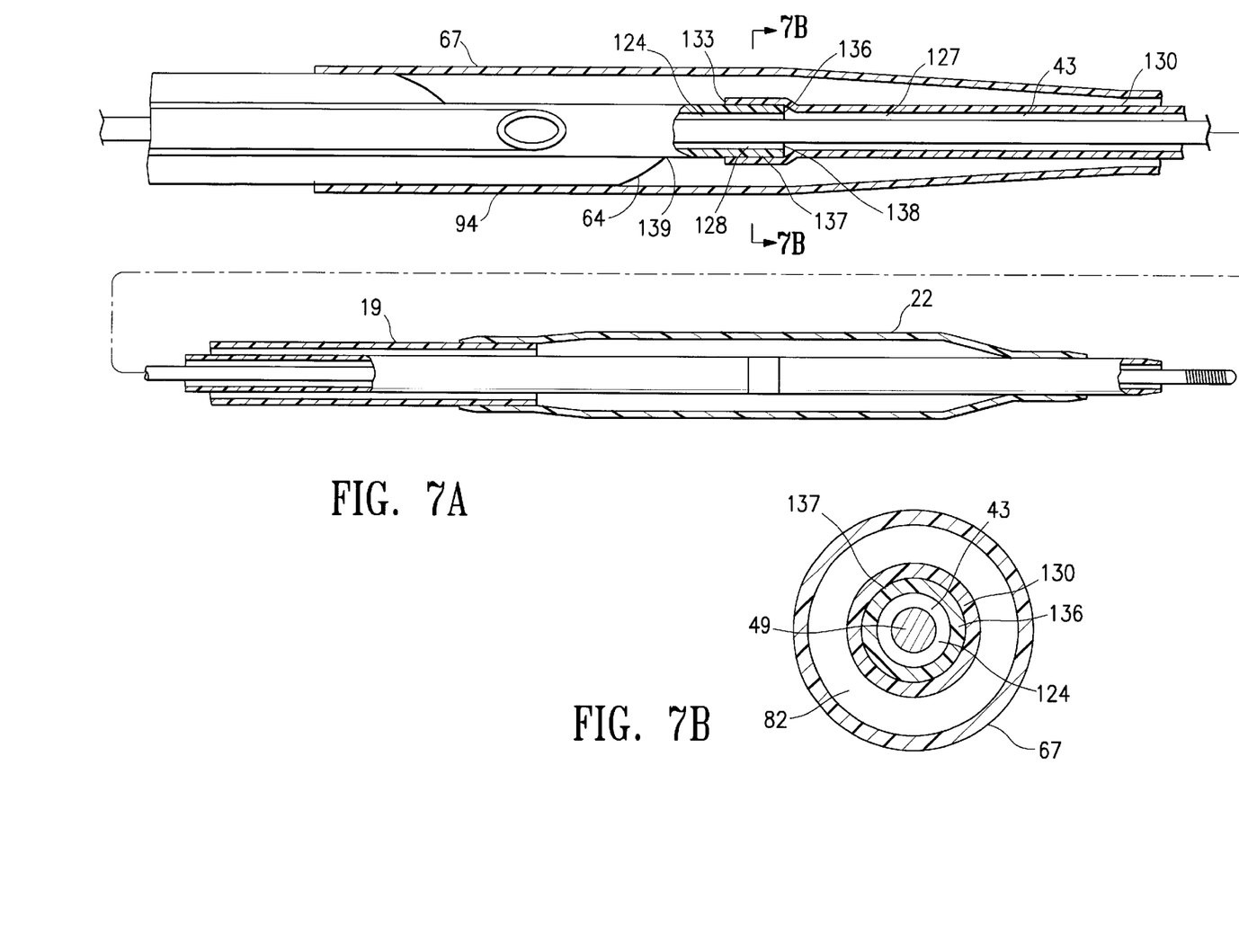
FIG. 7A is a is schematic, longitudinal cross sectional view of an alternate embodiment of the catheter of FIG. 1 along a portion of the distal shaft section.
FIG. 7B is a transverse cross sectional view of the catheter system of FIG. 7 taken along lines 7B—7B.

In an alternate embodiment, features of which illustrated in FIGS. 7A and 7B, the guidewire lumen 43, is formed of at least two lumens, proximal and distal guidewire lumens 124 and 127, respectively; fluidically connected at a point 128 within the outer tubular member 67 in the distal shaft section 19. The proximal guidewire lumen 124 is formed as part of the plurality of lumens 37, with the distal guidewire lumen 127 at the distal shaft section 19, formed of an inner tubular member 130. In the embodiment illustrated in FIG. 7, the inner tubular member 130 at a proximal extremity 133 is sealingly disposed about a distal extremity 136 of the proximal guidewire lumen 124, forming a seal 137. The seal 137 may be formed by adhesive or laser bond or the like, and is preferably, located along the first non-tapered portion 94 of the outer tubular member 67. Preferably, the seal 137 has a longitudinal dimension ranging from about 0.7 cm to about 0.3 cm, preferably from about 0.4 cm to about 0.5 cm, typically, 0.5 cm.

When the guidewire lumen 43 includes a proximal guidewire lumen 124 and an inner tubular member 130, a distal end 138 of the proximal guidewire lumen 124 is longitudinally set apart from a distal end 139 of the longest inflation lumen 64 in a range from about 0.5 cm to about 1.5 cm, preferably, from about 0.8 cm to about 1.2 cm, typically 1.0 cm.

Figures 8A, 8B:
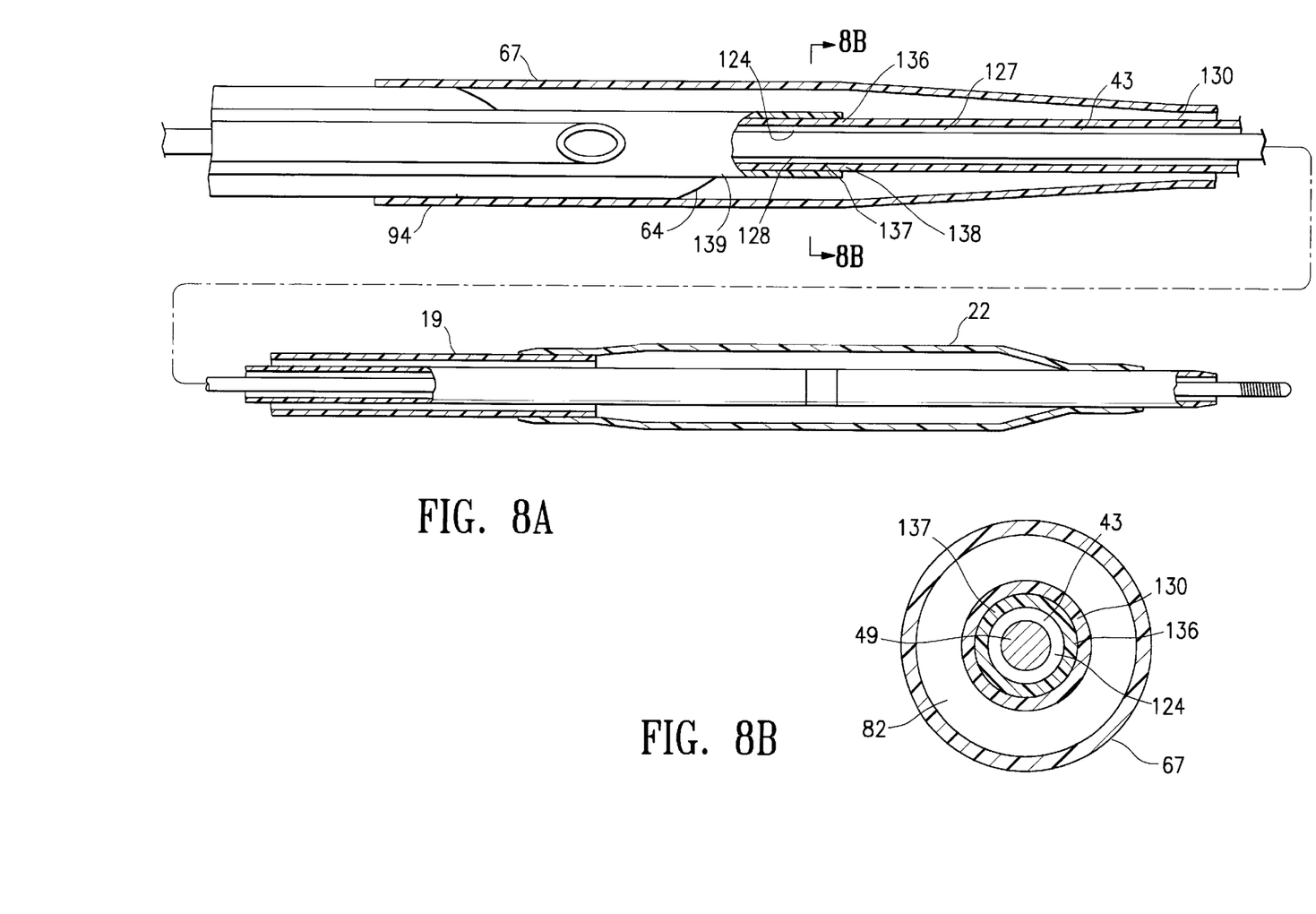
FIG. 8A is a schematic, longitudinal cross sectional view of an alternate embodiment of the catheter of FIG. 7A showing the inner tubular member extending along substantially the entire length of the proximal guidewire lumen.
FIG. 8B is a transverse cross sectional view of the catheter system of FIG. 8A taken along lines 8B—8B.

In an alternate embodiment, shown in FIGS. 8A and 8B, the inner tubular member 130 may extend along substantially the entire length of the proximal guidewire lumen 124. The inner tubular member 130 has a longitudinal dimension ranging from about 142 cm to about 152 cm, preferably, from about 149 cm to about 151 cm, typically about 150 cm; an outer diameter ranging from about 0.018 inch to about 0.028 inch, preferably, from about 0.018 inch to about 0.025 inch, typically about 0.018 inch; and an inner diameter ranging from about 0.014 inch to about 0.022 inch, preferably, from about 0.016 inch to about 0.018 inch, typically about 0.016 inch to 0.0165 inch.

Figure 9:
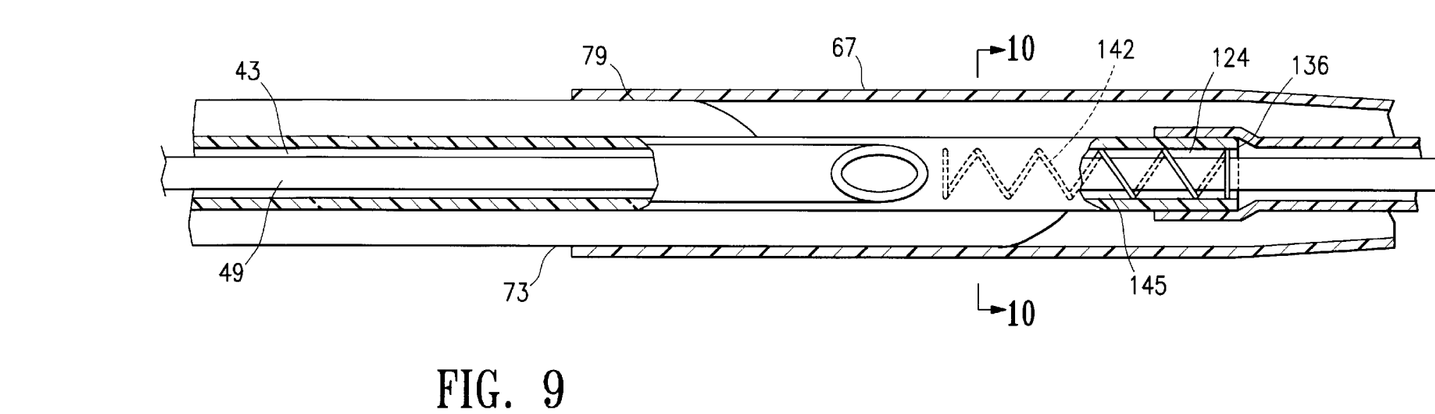
FIG. 9 is a schematic, enlarged, longitudinal cross sectional view of an alternate embodiment of the catheter of FIG. 7 along a portion of the distal shaft section showing the guidewire lumen including a coil member.
Figure 10:
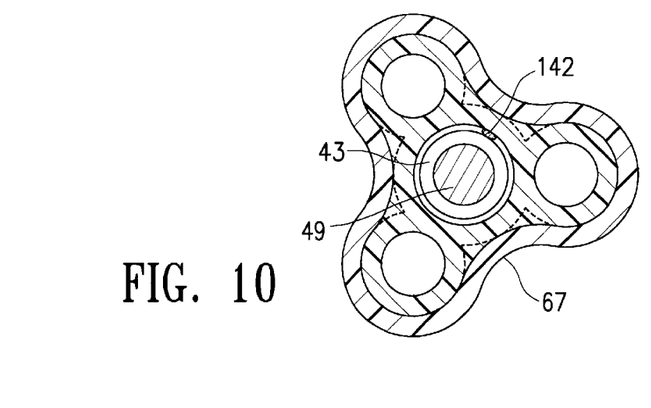
FIG. 10 is a transverse cross sectional view of the catheter system of FIG. 9 taken along lines 10—10.
Figures 11, 12:
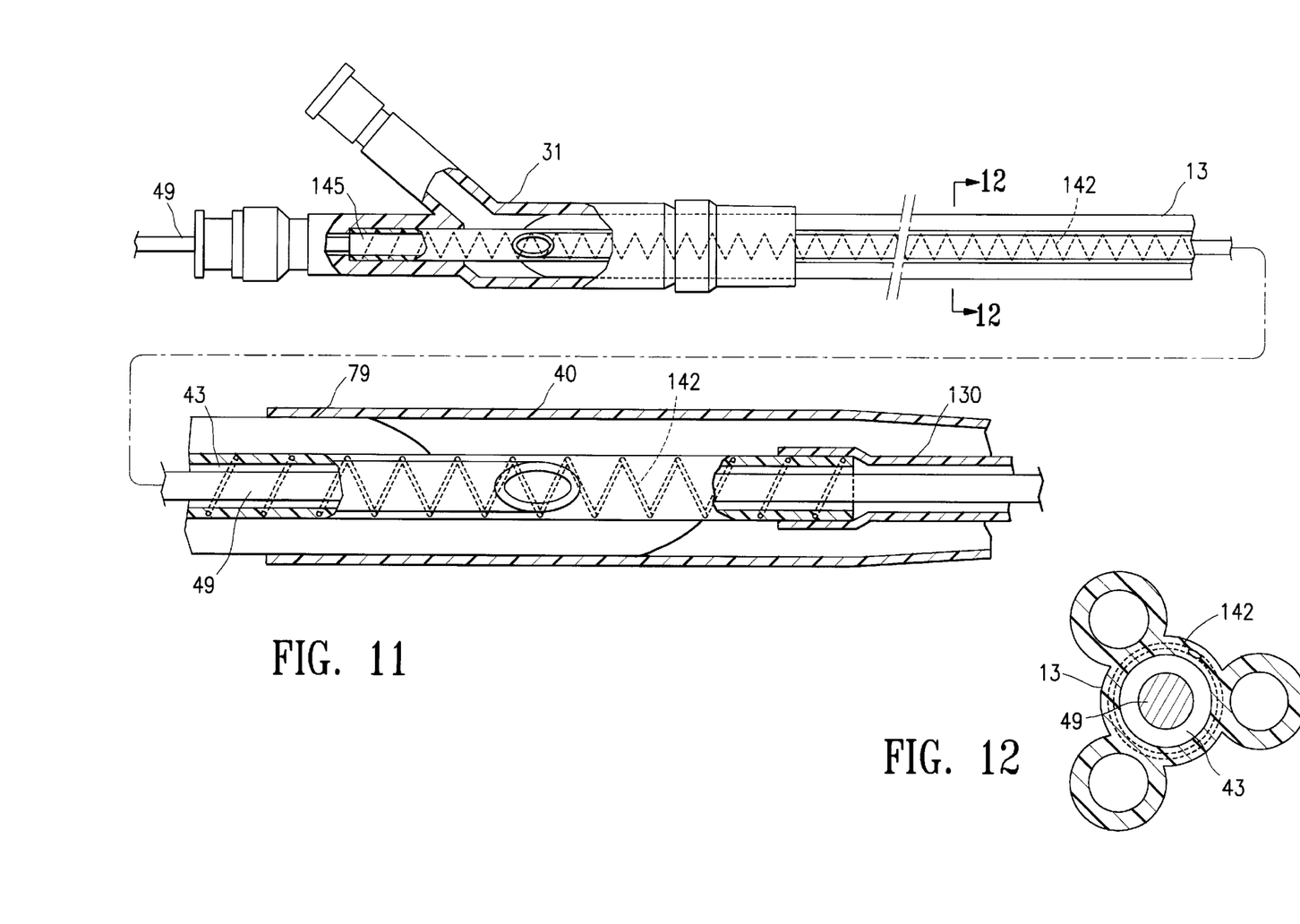
FIG. 11 is a schematic, enlarged, longitudinal cross sectional view of an alternate embodiment of the catheter of FIG. 10 showing the coil extending to the proximal end of the catheter shaft.
FIG. 12 is a transverse cross sectional view of the catheter system of FIG. 11 taken along lines 12—12.

Now referring to FIGS. 9 and 10, in yet another embodiment, a reinforcing member such as a coil member 142 is inserted into a portion of the guidewire lumen 43, such as a distal portion 145 of the proximal guidewire lumen 124 of FIG. 7. The coil member 142, preferably, extends proximally from the distal end 138 of the proximal guidewire lumen 124 to a point, preferably, distal to the seal 79 formed between the outer tubular member 67 and the distal extremity 73 of the proximal shaft section 16. In yet another embodiment, features of which are illustrated in FIGS. 11 and 12, the coil member 142 extends proximally to a proximal end 145 of the of the guidewire lumen 43.

The coil member 142, preferably, has a longitudinal dimension ranging from about 40 cm to about 120 cm, preferably, ranging from about 100 cm to about 115 cm, typically, 110 cm. Preferably, the coil has a pitch between the adjacent turns of typically 0.012 inch.

Figure 13:
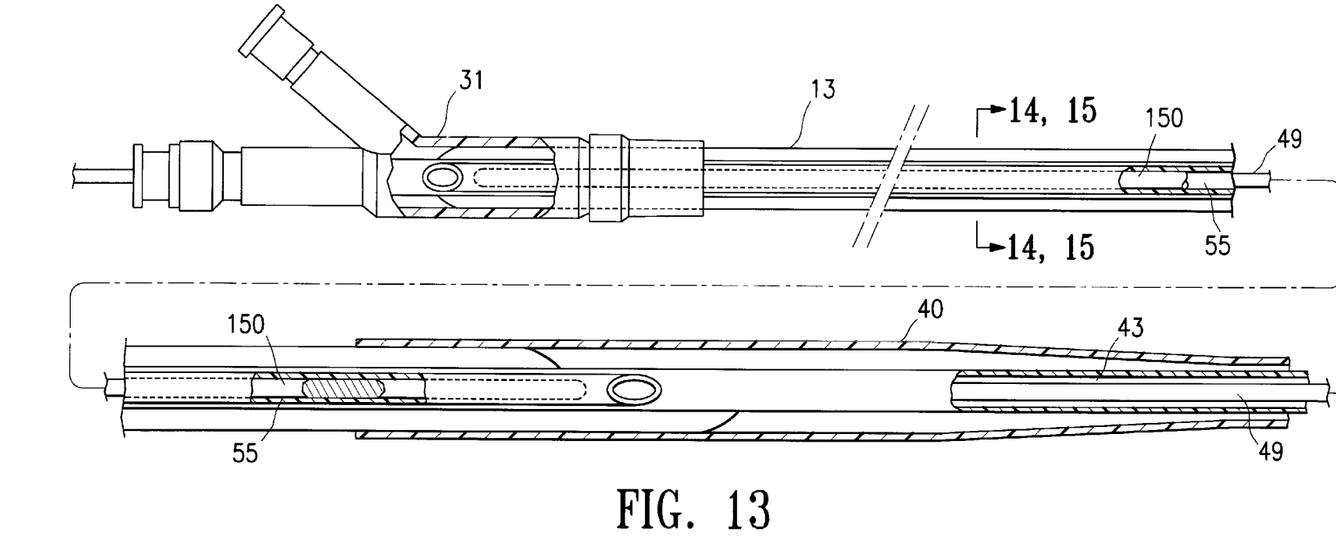
FIG. 13 is a schematic, enlarged, longitudinal cross sectional view of an alternate embodiment of the catheter of FIG. 7 showing a stiffening mandrel disposed along the interior of one of the inflation lumens.
Figure 14:
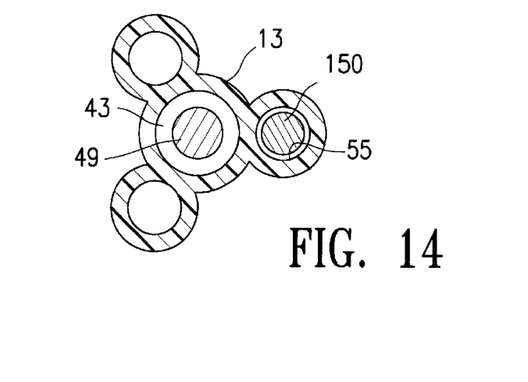
FIG. 14 is a transverse cross sectional view of the catheter system of FIG. 13 taken along lines 14—14.

In yet another embodiment features of which are illustrated in FIGS. 13 and 14, a stiffening mandrel 150, metallic or polymeric, may be disposed along the interior of one of the inflation lumens 55. Preferably, the stiffening mandrel is loosely fitted within the host inflation lumen.

Figure 15:
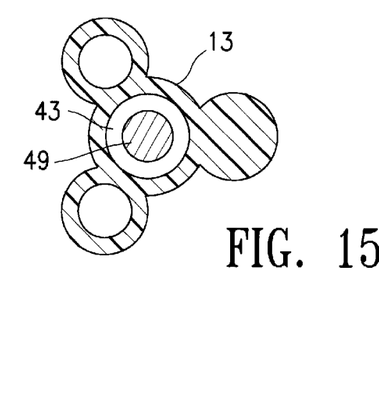
FIG. 15 is a transverse cross sectional view of an alternate embodiment of the catheter system of FIG. 13 taken along lines 15—15 showing one of the lumens having a solid interior.

In an alternate embodiment, features of which are shown in FIG. 15, one of the non-guide wire lumens 52' is a solid member.

Figure 16:
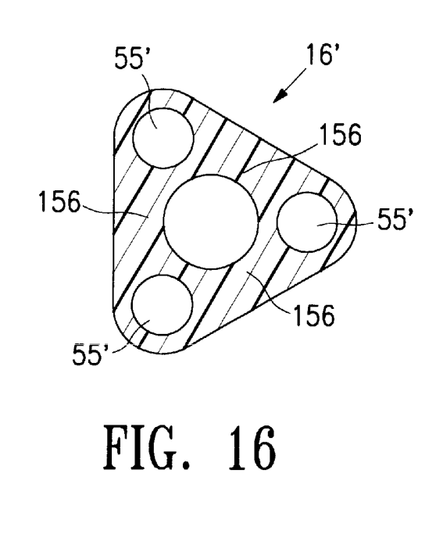
FIG. 16 is a transverse cross sectional view of an alternate embodiment of the catheter system of FIG. 1 showing the proximal catheter shaft having a solid wall thickness between the adjacent non-guidewire lumens.

Now referring to FIG. 16, the proximal shaft section 16' has an outer surface 153 with a solid wall thickness 156 between the adjacent inflation lumens 55' (i.e., no gap).

Figure 17:
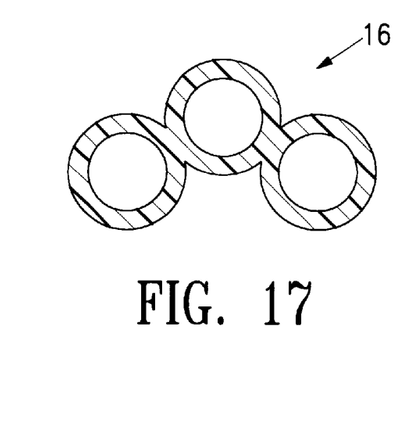
FIG. 17 is a transverse cross sectional view of an alternate embodiment of the catheter system of FIG. 1 taken along lines 17—17 showing the proximal catheter shaft including three lumens.
Figure 18:
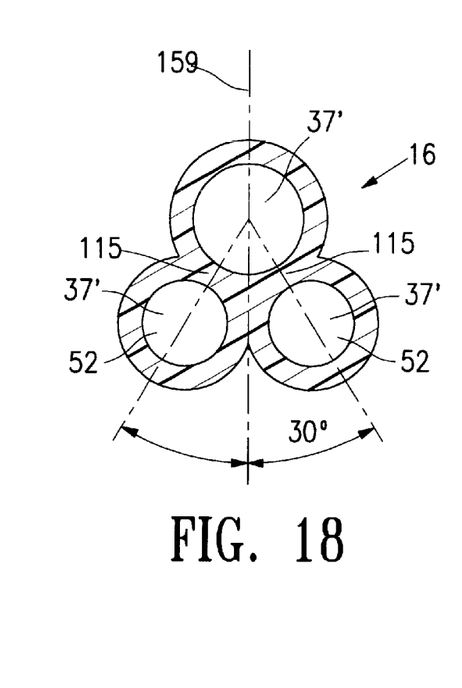
FIG. 18 is a transverse cross sectional view of an alternate embodiment of the catheter system of FIG. 1 taken along lines 18—18.

In yet another embodiment, features of which are illustrated in FIGS. 17–18, the proximal shaft section 16" includes three lumens 37", one of which is a guidewire lumen 43" and the others are non-guidewire lumens 52", including at least one inflation lumen 55". The non-guidewire lumens 52" are disposed about the guidewire lumen 43, each in a different transverse plane. Preferably, the non-guidewire lumens 52" are circumferentially disposed about the guidewire lumen 43" providing a substantially balanced distribution of weight on the transverse dimension of the proximal shaft section 16". The non-guidewire lumens 52", preferably as shown in FIG. 18, are 30° off a longitudinal axis 159" of the proximal shaft section 16", with the guidewire lumen 43" having a longitudinal axis 162" extending substantially parallel to the longitudinal axis 159" of the proximal shaft section 16". At least a portion of a thickness 115" for each of the inflation lumens 37" is shared with the thickness of the other two lumens.

Figures 19, 20, 21:
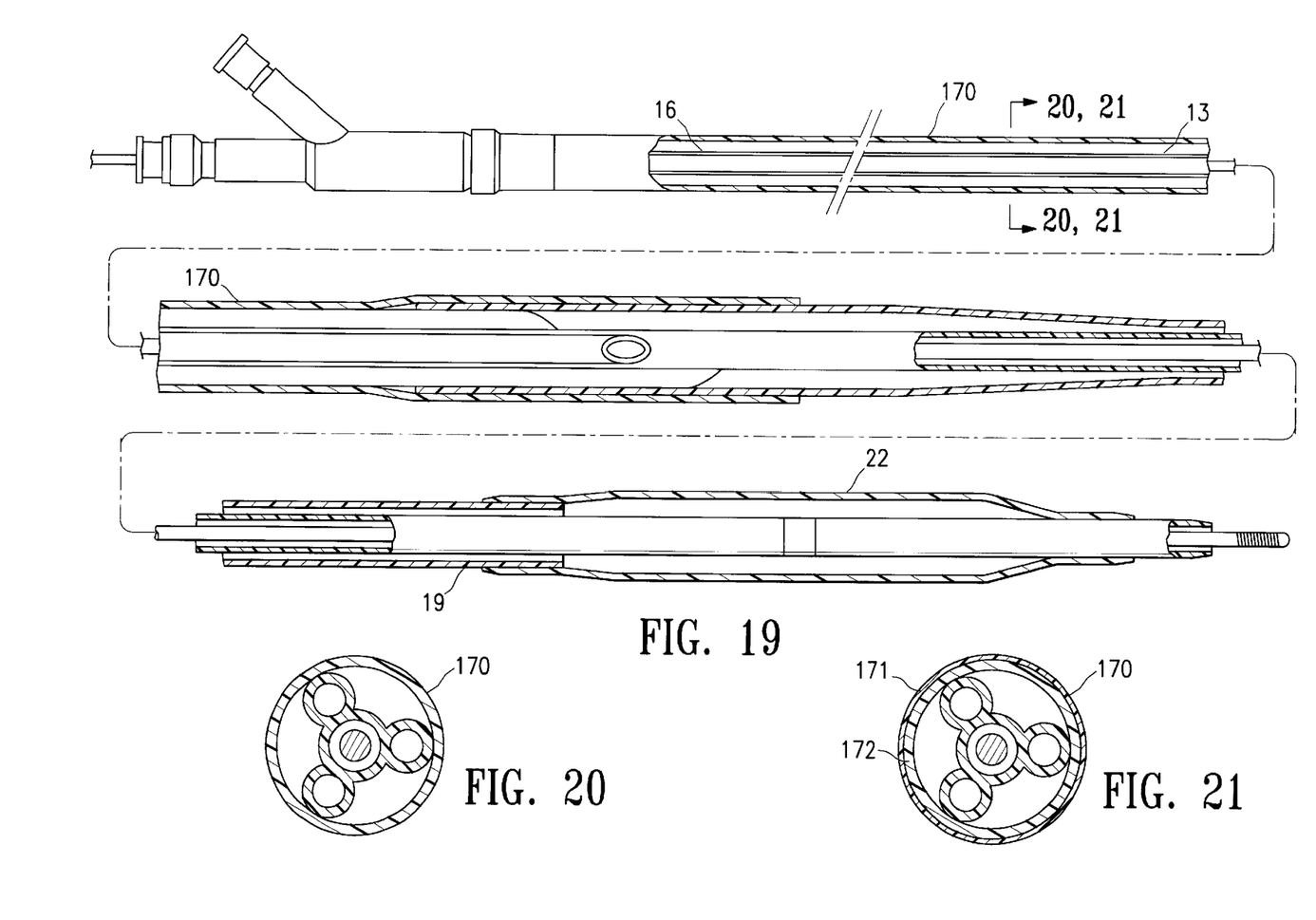
FIG. 19 is a schematic, enlarged, longitudinal cross sectional view of an alternate embodiment of the catheter of FIG. 1 showing an exterior jacket disposed along at least a portion of the catheter shaft.
FIG. 20 is a transverse cross sectional view of the catheter system of FIG. 19 taken along lines 20—20.
FIG. 21 is a transverse cross sectional view of an alternate embodiment of catheter system of FIG. 19 taken along lines 21—21.

Optionally, as shown in FIGS. 19 and 20, at least a portion of the proximal and distal shaft sections, 16 and 19, respectively, may include an exterior jacket 170.

The proximal shaft section 16 may be formed of Nylon 12; polyether block amides available under the trade name Pebax from Atochem; polyurethanes; polyester block copolymers (containing one or more of the following glycols) comprising hard segments of polyethylene-terephthalate or polybutylene-terephthalate, and soft segments of polyether such as polyethylene glycol, polypropylene glycol or polytetramethylene glycol ethers, such as those available under the trade name Hytrel from DuPont; polyesters available from Dutch State Mines under the trade name Arnitel; or blends thereof.

The outer tubular member 67 may be formed of a polymeric material, including nylons; polyether block amides such as Pebax; polyurethanes; polyester block copolymers (containing one or more of the following glycols) comprising hard segments of polyethylene-terephthalate or polybutylene-terephthalate, and soft segments of polyether such as polyethylene glycol, polypropylene glycol or polytetramethylene glycol ethers, such as those available under the trade name Hytrel; polyesters under the trade name Arnitel; or blends thereof. The outer tubular member 67 is preferably formed at least in part of Nylon 12.

The inner tubular member 130 may be formed from a lubricious material such as high density polyethylene, polyimide, PEEK, or a braided combination thereof, and preferably, is of a tri-layer tubular construction including high density polyethylene as an inner layer, a copolymer of ethylene and acrylic acid such as Primacor from Dow Chemical Co. as a middle layer, and a nylon as the outer layer.

The coil member 142 and the stiffening mandrel 150 may, independently, be formed of a metallic material, and are preferably, formed of 304v stainless steel, NiTi alloy, MP35N, Elgiloy and the like. Non-metallic materials may also be used such as braided polyimide, and high strength polymers such as polyetheretherketone (PEEK), polyetherketone, and polyketone.

The exterior jacket 170 may be formed of any nylon, polyether block amides such as Pebax, copolymers of ethylene and acrylic acid such as Primacor from Dow Chemical Co., and polyolefins such as Plexar from Equistar Chemical Co., or any combination thereof. The exterior polymeric jacket 170 is preferably formed at least in part of nylon. Preferably, the jacket 170, as shown in FIG. 21, has a two layered structure, an outer layer 171 being relatively lubricious to facilitate advancement of the catheter through the lumen of a guiding catheter, other lumens and ports, and an inner layer 172 being of high strength to withstand the pressures of the inflation fluid.

The balloon 22 may be formed of suitable compliant, non-compliant, or hybrid compliant material, including thermoplastic and thermosetting polymers depending upon the end use, e.g. dilatation, stent delivery etc. The presently preferred balloon polymeric material is a relatively compliant polyether block amide such as Pebax 70 sold by Elf Atochem. Other materials include Nylon 11 and 12 and Pebax 72. Compliant polymeric materials, i.e. compliant within the working expansion of the balloon, which provide a wingless balloon and which have substantially elastic recoil during deflation are also suitable for stent delivery work. Other desirable polymeric materials for balloon manufacture include polyurethanes such as TECOTHANE.

Figure 22:
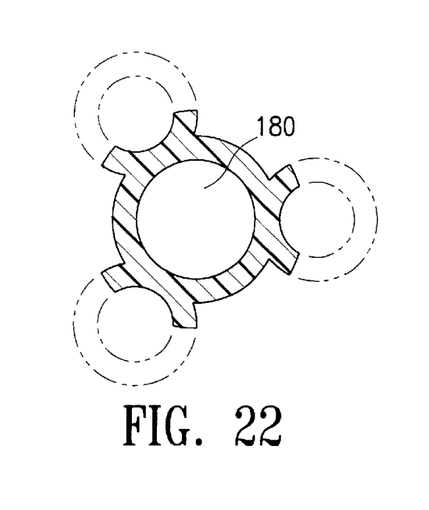
FIG. 22 is a transverse cross sectional view of the multi lumens of FIG. 1 after the lumens are first trimmed.
Figure 23:
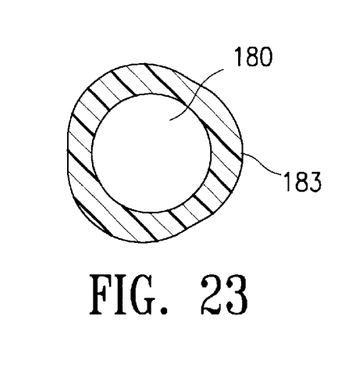
FIG. 23 is a transverse cross sectional view of the multi lumens of FIG. 22 showing the exterior surface of the guidewire lumen after reshaping.
Figure 24:
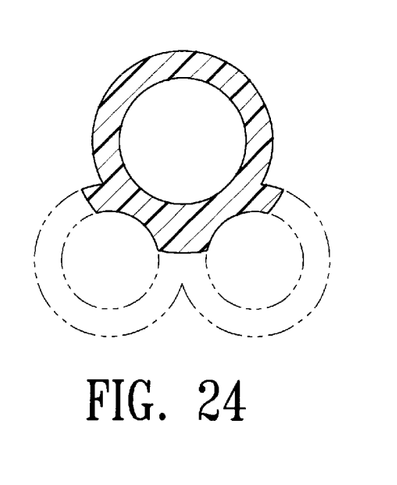
FIG. 24 is a transverse cross sectional view of the multi lumens of FIG. 18 after the lumens are first trimmed.
Figure 25:
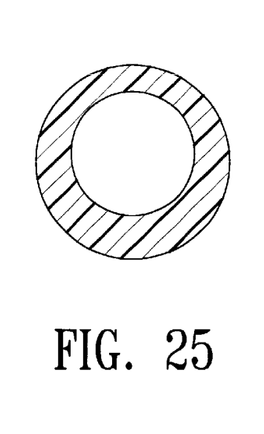
FIG. 25 is a transverse cross sectional view of the multi lumens of FIG. 24 showing the exterior surface of the guidewire lumen after reshaping.

By way of forming the multi-lumen proximal shaft section 16 of the present invention, a multi-lumen shaft is first extruded. The various lumens 37 are then trimmed, preferably at an angle, longitudinally by first inserting a mandrel into the other lumens which may be adversely affected during the trimming process. The exterior surface of the guidewire lumen 180 is then reshaped (e.g. using heat) to smooth the exterior surface 183 as seen in FIGS. 22 and 23. The catheter shaft assembly, is then constructed according to conventional techniques. Similarly, FIGS. 24 and 25, show a similar process for the alternate catheter of FIG. 18.

It will be apparent from the foregoing that, while particular forms of the invention have been illustrated and described, various modifications can be made without departing from the spirit and scope of the invention. Moreover, those skilled in the art will recognize that features shown in one embodiment may be utilized in other embodiments.

What is claimed is:

1. An intravascular catheter, comprising:
   an elongated shaft having proximal and distal ends;
   a proximal shaft section having a plurality of tubular members forming non-concentric lumens with at least one lumen forming at least a portion of a guidewire receiving lumen, and at least one lumen forming at least a portion of an inflation lumen;
   a distal shaft section including an outer tubular member having a proximal extremity disposed about and securely attached to a distal extremity of the proximal shaft section, at least a portion of the guidewire receiving lumen extending along at least a portion of the distal shaft section distally to the shaft distal end, and at least a portion of the inflation lumen extending along at least a portion of the distal shaft section to a point proximal to the shaft distal end; and
   an inflatable member disposed on the distal shaft section and having proximal and distal ends and an interior chamber in fluid communication with the inflation lumen.

2. The catheter of claim 1, wherein the proximal extremity of the outer tubular member forms a seal with at least a portion of each of the proximal shaft lumens.

3. The catheter of claim 1 wherein all of the proximal shaft lumens except the guidewire receiving lumen are non-guidewire lumens circumferencially disposed about the guidewire lumen.

4. The catheter of claim 3 wherein the transverse centers of the non-guidewire receiving lumens form a triangular arrangement.

5. The catheter of claim 1, 3, or 4 wherein the proximal shaft section includes at least three non-concentric lumens.

6. The catheter of claim 5 wherein the proximal shaft section includes at least four non-concentric lumens.

7. The catheter of claim 3 wherein the non-guidewire receiving lumens are inflation lumens.

8. The catheter of claim 3 wherein the non-guidewire receiving lumens are longitudinally set apart.

9. The catheter of claim 8 wherein the guidewire receiving lumen extends distally beyond the non-guidewire receiving lumens.

10. The catheter of claim 3 wherein the distal shaft section includes an inner tubular member extending along at least a portion of the outer tubular member to the shaft distal end, and forming at least a portion of the guidewire receiving lumen in the distal shaft section and defining with the outer tubular member at least a portion of the inflation lumen.

11. The catheter of claim 10 wherein the guidewire receiving lumen includes a proximal guidewire receiving lumen, and a distal guidewire receiving lumen formed by the inner tubular member in the distal shaft section, the proximal and the distal guidewire lumens being in fluid communication with one another.

12. The catheter of claim 11 wherein a proximal extremity of the inner tubular member is sealingly disposed about a distal extremity of the proximal guidewire lumen and forming a junction therebetween.

13. The catheter of claim 11 wherein the inner tubular member extends proximally within the proximal guidewire receiving lumen to the shaft proximal end.

14. The catheter of claim 10 wherein a reinforcing member extends within at least a portion of the guidewire receiving lumen.

15. The catheter of claim 14 wherein the reinforcing member extends within at least a portion of the guidewire receiving lumen extending in the distal shaft section.

16. The catheter of claim 3 wherein the outer tubular member is tapered in the distal direction.

17. The catheter of claim 16 wherein the outer tubular member taper is in steps.

18. The catheter of claim 16 wherein the outer tubular member taper is continuous.

19. The catheter of claim 12 wherein the junction between the inner tubular member and the proximal guidewire lumen is in an area within the outer tubular member having a non-tapered length.

20. An intravascular catheter, comprising:
   an elongated shaft having proximal and distal ends;
   a proximal shaft section having at least three non-concentric lumens with at least one lumen forming at least a portion of a guidewire receiving lumen, and at least one lumen forming at least a portion of an inflation lumen;
   a distal shaft section including an outer tubular member having a proximal extremity disposed about and securely attached to a distal extremity of the proximal shaft section, at least a portion of the guidewire receiving lumen extending along at least a portion of the distal shaft section distally to the shaft distal end, and at least a portion of the inflation lumen extending along at least a portion of the distal shaft section to a point proximal to the shaft distal end; and an inflatable member disposed on the distal shaft section and having proximal and distal ends and an interior chamber in fluid communication with the inflation lumen.

* * * * *